Figure 1:
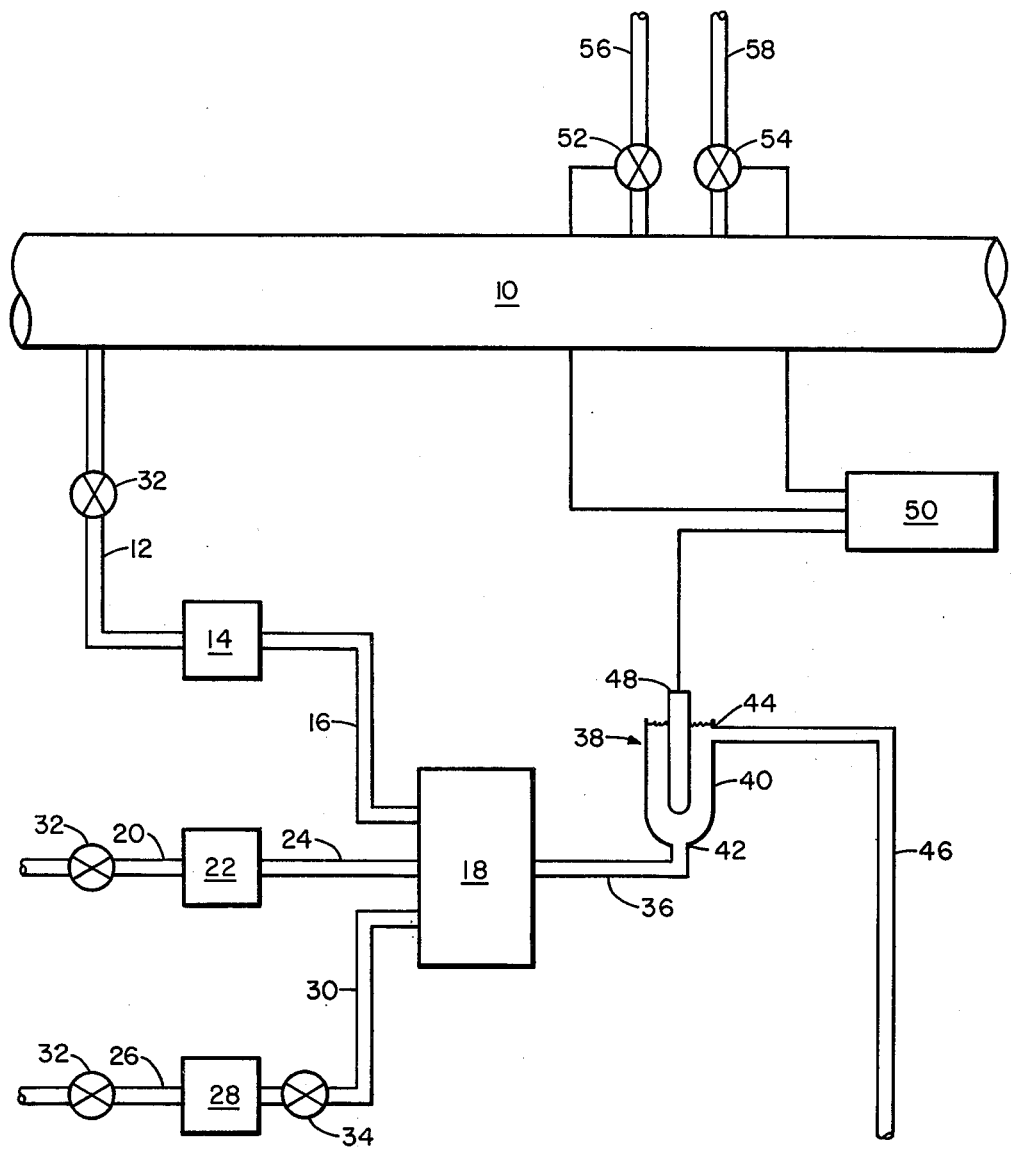

United States Patent [19]
Wimberley

[11] 3,980,435
[45] Sept. 14, 1976

[54] METHOD FOR CONTROLLNG BORIC ACID CONCENTRATION IN AN AQUEOUS STREAM

[75] Inventor: Jerry W. Wimberley, Ponca City, Okla.

[73] Assignee: Continental Oil Company, Ponca City, Okla.

[22] Filed: Sept. 2, 1975

[21] Appl. No.: 609,451

[52] U.S. Cl............................ 23/230 R; 260/617 H; 423/276
[51] Int. Cl.²......................................... G01N 31/00
[58] Field of Search ............... 252/1; 423/280, 276; 23/230 R

[56] References Cited
UNITED STATES PATENTS 3,729,545  4/1973  Castin et al........................ 423/280

OTHER PUBLICATIONS

The Condensed Chemical Dictionary, Reinhold Pub. Corp., New york, 1956, p. 167.

*Primary Examiner*—Leland A. Sebastian
*Attorney, Agent, or Firm*—F. Lindsey Scott

[57] ABSTRACT

A method for maintaining a desired boric acid concentration in an aqueous stream by mixing a selected quantity of the aqueous stream with an aqueous solution containing an alkali metal hydroxide in an amount stoichiometrically equal to the amount of boric acid which would be present in the selected quantity of the aqueous stream at the desired boric acid concentration and thereafter determining the pH of the solution and adjusting the boric acid concentration in the aqueous stream in response to the pH determination.

4 Claims, 2 Drawing Figures

METHOD FOR CONTROLLNG BORIC ACID CONCENTRATION IN AN AQUEOUS STREAM

This invention relates to the control of boric acid concentration in aqueous streams.

In many process streams it is desirable to control the acid concentration or other parameters of aqueous streams. Some such process streams occur in processes for the oxidation of paraffinic materials to produce alcohols and the like wherein boric acid is used in the oxidation process. Some such processes are shown in U.S. Pat. No. 3,475,500 issued Oct. 28, 1969 to Russell; U.S. Pat. No. 3,594,422 issued July 20, 1971 to Golden et al.; British Pat. No. 944,110 published Dec. 11, 1963; British Pat. No. 1,017,214 published Jan. 19, 1966; British Pat. No. 1,110,396 published Apr. 18, 1968 and British Pat. No. 1,035,624 published July 13, 1966. In such processes it is desirable in many instances to control the boric acid concentration in an aqueous stream. The control of such streams containing acids has been achieved heretofore by periodic titrations, by colorimeteric methods, and the like. Such methods have certain drawbacks. For instance, the use of titrations results in intervals between titrations so that it is possible for the acid concentration to vary substantially between pH determinations and the like. The use of colorimetric methods requires elaborate dilution techniques and is further subject to the presence of contaminants in the aqueous streams which could render the streams opaque to some extent. Since in many instances it is desirable to control the acid in aqueous streams precisely and substantially continuously, a continuing effort has been directed to the development of a method which will substantially continuously maintain a desired acid concentration in an aqueous stream.

It is an object of the present invention to provide a method whereby an aqueous boric acid stream may be substantially continuously monitored to maintain a desired boric acid concentration in the aqueous stream.

Figure 2:
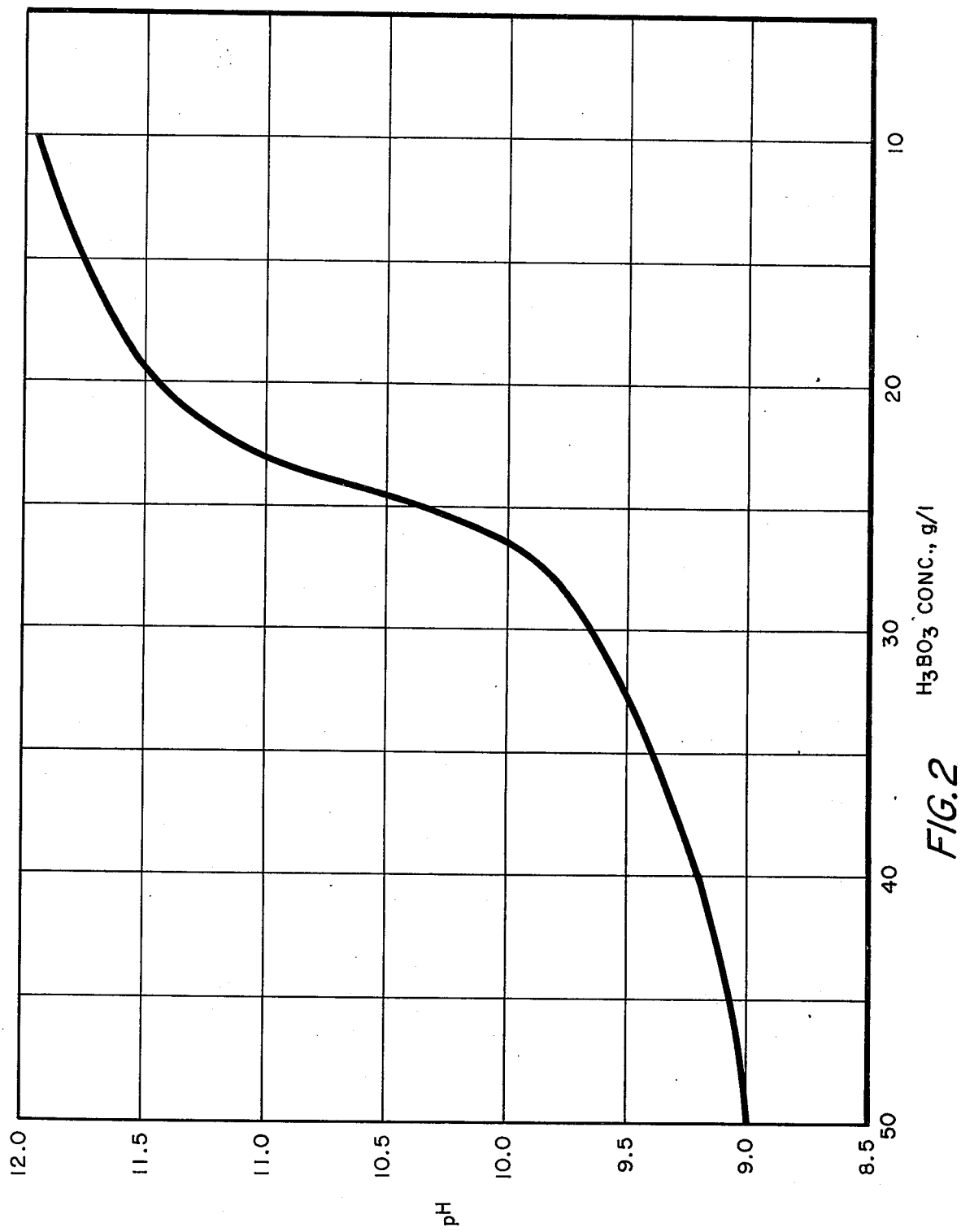

It has now been found that the objective of the present invention is achieved by the use of a method for substantially continuously maintaining a desired boric acid concentration in an aqueous stream wherein the method consists essentially of:

a. mixing a selected quantity of the aqueous stream with an aqueous solution containing an alkali metal hydroxide in an amount substantially stoichiometrically equal to the amount of boric acid which would be present in the selected quantity of the aqueous stream at the desired boric acid concentration to form a solution mixture;

b. determining the pH of said mixture; and c. adjusting the boric acid concentration in the aqueous solution in response to the pH determination to the desired boric acid concentration FIG. 1 is a schematic diagram of a process control system wherein the method of the present invention is used to control the boric acid concentration in an aqueous stream; and FIG. 2 shows the variation in pH as varying amounts of boric acid are added to a sodium hydroxide solution.

In the description of FIG. 1 the same numbers will be used to describe the same or similar components throughout.

With reference to FIG. 1, a pipe 10 containing an aqueous solution of boric acid is shown. A sample pipe 12 is positioned in fluid communication with pipe 10 and a proportioning pump 14. Proportioning pump 14 is connected to a mixer 18 by a pipe 16 to provide fluid communication between pipe 10 and mixer 18 through pipe 12, pump 14, and pipe 16. An alkaline solution line 20 is shown fluidly communicating a proportioning pump 22 which is in fluid communication with mixer 18 through pipe 24. A water line 26 is also shown in fluid communication with a proportioning pump 28 which is in fluid communication with mixer 18 through pipe 30. Pipe 30 also includes a valve 34, since the flow of water to mixer 18 is optional. Valves 32 are positioned in lines 12, 20, and 26 to allow the shut-off of fluid to proportioning pumps 14, 22, and 28. Mixer 18 is connected to a pH analyzer 38 through a mixer outlet 36. pH analyzer 38 is shown as a cup 40 having an inlet 42 at the lower portion of cup 40 and an outlet 44 at the upper portion of cup 40. Outlet 44 is connected to a drain 46 for disposal of the solution after analysis. An electrode 48 is positioned in cup 40 and is operatively connected to a controller 50. Controller 50 is operatively connected to a boric acid line valve 52 and a water line valve 54 which are positioned in a boric acid line 56 and a water line 58, respectively. Boric acid line 56 and water line 58 are in fluid communication with pipe 10 so that the boric acid concentration in the aqueous solution flowing inside pipe 10 can be controlled.

In the operation of the apparatus shown in FIG. 1, a sample of the aqueous boric acid solution in pipe 10 is withdrawn through sample line 12 and proportioning pump 14 at a precisely controlled rate and passed through pipe 16 to mixer 18 substantially continuously. Simultaneously, a standardized alkaline solution is passed through line 20, proportioning pump 22, and line 24 to mixer 18 at a precisely controlled rate. In the event that it is desired to dilute the mixture of alkaline solution and boric acid solution, water is passed through line 26, proportioning pump 28, and line 30 to mixer 18 at a precisely controlled rate. The three streams are mixed in mixer 18 and passed to pH analyzer 38 where the pH is determined. The solution flows into the bottom of cup 40 through inlet 42 and out of cup 40 through outlet 44 and drain 46 to waste. The pH analyzer electrode 48 provides an indication of the pH of the solution which is used to provide an input signal to controller 50 which controls valves 52 and 54 in response to the pH so that additional boric acid or additional water can be added to the aqueous stream in line 10 to provide a boric acid stream having a controlled boric acid concentration.

Desirably, the boric acid sample selected is mixed with a quantity of standardized alkaline solution which contains an alkali metal hydroxide in an amount stoichiometrically equivalent to that amount of boric acid which would be in the selected quantity of the aqueous stream at the desired boric acid concentration. More specifically, in the instance wherein the selected quantity of aqueous stream desirably contains 1.0 equivalents of boric acid, it is desirable that the alkaline metal hydroxide solution also contain 1.0 equivalents of alkali metal hydroxide. Such a ratio provides increased accuracy in the pH determination and allows for adjustments much more quickly than were different ratios of acid and alkaline material present. Suitable alkali metal hydroxides are sodium hydroxide, potassium hydroxide, and the like. Particularly desirable results have been achieved wherein sodium hydroxide was used. The term "aqueous stream" as used herein includes not only streams comprising primarily water and boric acid but also water streams containing varying amounts of organic materials other than boric acid, such as alkanols containing up to about 4 carbon atoms and the like. Such organic materials may be present in amounts up to about 50 weight percent. For instance, lower alkanols, such as methanol and ethanol, are often used as solubilizers to increase the solubility of boric acid in such aqueous streams.

The determination of the pH may be by means known to those skilled in the art. However, it has been found that very desirable results were achieved wherein a Sargent combination electrode No. S-30072-15[1] and a Corning Digital pH meter No. 112[2] were used. Quite obviously, other arrangements could be used to determine the pH of the mixture so long as the pH is determined continuously and so long as a suitable signal is generated for use with the particular controller selected. It is to be understood that the pH measurement can be reported as a solution potential with reference to a particular base electrode. Such potentials are reported hereafter in the examples as a negative potential, and such information is considered to be the substantial equivalent of a pH determination, since quite obviously the boric acid concentration can be controlled equally well using either signal.

[1]A combination electrode marketed by E. H. Sargent & Co., Chicago, Illinois.
[2]A pH meter manufactured by Corning Glass Works, Medfield, Mass.

The proportioning pumps are of any type known to those skilled in the art for pumping a stream of carefully controlled volume at a steady flow rate. Since such equipment is well known to those skilled in the art as are suitable mixers, it is believed that no further discussion is necessary with respect to these particular items. Similarly, controllers and controlled valves which are responsive to such controllers are known to those skilled in the art and need not be discussed further since the primary novelty of the present invention lies in the method for maintaining the desired boric acid concentration in an aqueous stream.

Having thus described certain preferred embodiments of the present invention, it is pointed out that the described embodiments are illustrative rather than limiting in nature and that many variations and modifications are possible within the scope of the invention. It is expected that many such variations and modifications may appear obvious or desirable to those skilled in the art upon a review of the foregoing description of preferred embodiments and the following example.

EXAMPLE

To each of nine 100-ml volumetric flasks were added 40 ml of 0.1 N sodium hydroxide solution. 10 ml of boric acid solutions of varying concentrations from 10 to 50 g of boric acid per liter were then added to each of the nine flasks, and thereafter the flasks were diluted to 100 ml with deionized water. The flasks were then shaken well and the pH and potential of each of the solutions was then measured. Table I contains the data, and FIG. 1 shows the data in graphic form. From the graph, it is clear that at a boric acid concentration of about 25 grams per liter, a pH change of ±0.3 pH units is achieved by varying the boric acid concentration from 25 to 26 or from 25 to 24 grams per liter of boric acid. At a boric acid concentration of 25 grams per liter, the boric acid added contains 4.04 milliequivalents of boric acid. This is substantially stoichiometrically equivalent to the 4.0 equivalents of sodium hydroxide added. It is clear then that it is desirable in order to have the greatest pH variation per unit variation in the boric acid stream that the selected sample be mixed with an aqueous solution containing an alkali metal hydroxide in an amount which is stoichiometrically equal to the amount of boric acid expected in the selected sample.

TABLE I

| $H_3BO_3$ Concentration (g/l) | pH | Millivolts |
| --- | --- | --- |
| 50 | 8.98 | −121.8 |
| 40 | 9.21 | −135.4 |
| 30 | 9.66 | −161.6 |
| 28 | 9.81 | −170.3 |
| 26 | 10.09 | −187.1 |
| 24 | 10.70 | −222.6 |
| 22 | 11.22 | −252.7 |
| 20 | 11.48 | −268.5 |
| 10 | 11.96 | −297.2 |

It is believed clear from the foregoing example and the description of the preferred embodiments that Applicant has discovered a highly reliable and a highly accurate method for maintaining a desired boric acid concentration in an aqueous stream containing boric acid.

Having thus described the invention, I claim:

1. A method for substantially continuously maintaining a desired boric acid concentration in an aqueous stream, said method consisting essentially of:
   a. mixing a selected quantity of said aqueous stream with an aqueous solution containing an alkali metal hydroxide in an amount substantially stoichiometrically equal to the amount of boric acid which is present in said selected quantity of said aqueous stream at said desired boric acid concentration to form a solution mixture;
   b. determining the pH of said mixture; and
   c. adjusting the boric acid concentration, in said aqueous stream in response to said determination, to said desired boric acid concentration.

2. The method of claim 1 wherein said alkali metal hydroxide is sodium hydroxide.

3. The method of claim 1 wherein said mixture is diluted to a desired concentration with water.

4. The method of claim 1 wherein said pH is between 9.5 and 11.5.

* * * * *